US00PP28794P2

(12) United States Plant Patent
Wood

(10) Patent No.: US PP28,794 P2
(45) Date of Patent: Dec. 26, 2017

(54) ***BUDDLEIA* PLANT NAMED 'SMNBDBT'**

(50) Latin Name: *Buddleia davidii*
Varietal Denomination: SMNBDBT

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,699

(22) Filed: Oct. 28, 2016

(51) Int. Cl.
*A01H 5/00* (2006.01)

(52) U.S. Cl.
USPC ..... Plt./242

(58) Field of Classification Search
USPC ..... Plt./242
CPC ..... A01H 5/00; A01H 5/02
See application file for complete search history.

*Primary Examiner* — Kent L Bell
(74) *Attorney, Agent, or Firm* — Cassandra Bright

(57) ABSTRACT

A new and distinct *Buddleia* cultivar named 'SMNBDBT' is disclosed, characterized by a compact plant habit that is dense, round and outwardly spreading. Plants have an overall height of less than two feet. Stems are thick and chunky with short internodes, leaves are coriaceous. Plants are cold-hardy and produce abundant panicles of purple flowers. The new variety is a *Buddleia*, normally produced as an outdoor garden or container plant.

3 Drawing Sheets

Latin name of the genus and species: *Buddleia davidii*.
Variety denomination: 'SMNBDBT'.

BACKGROUND OF THE INVENTION

The new *Buddleia* cultivar is a product of a planned breeding program conducted by the inventor, Timothy D. Wood, in Grand Haven, Mich., USA. The objective of the breeding program was to produce compact plants with strong branches in a range of flower colors. The cross resulting in this new variety was made during 2012.

The seed parent is the unpatented, proprietary *Buddleia davidii* 'UC 596'. The pollen parent is the unpatented *Buddleia davidii* 'Adonis Blue'. The new variety was discovered in 2013 by the inventor in a group of seedlings resulting from the 2012 crossing, in Grand Haven, Mich., USA.

Asexual reproduction of the new cultivar was performed by softwood stem cuttings. This was first performed in Grand Haven, Mich., USA in 2013 and has shown that the unique features of this cultivar are stable and reproduced true to type in 6 successive generations.

SUMMARY OF THE INVENTION

The cultivar 'SMNBDBT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNBDBT' These characteristics in combination distinguish 'SMNBDBT' as a new and distinct *Buddleia* cultivar:

1. Compact, dense plants less than two feet tall. Habit is spreading and plants are somewhat flat-topped.
2. Thick, chunky stems with short internodes.
3. Heavy, coriaceous, textured leaves.

4. Numerous panicles of purple flowers.
5. Cold hardiness comparable to the most cold-hardy *Buddleia davidii* on the market.
6. Plants less than 2 feet tall.
7. Compact and rounded plant habit.

Plants of the new cultivar 'SMNBDBT' are similar to plants of the seed parent, *Buddleia davidii* 'UC 596' in most horticultural characteristics, however, plants of the new cultivar 'SMNBDBT' differ in the following;

1. The new cultivar has a larger plant size.
2. The new variety produces larger panicles.
3. The new variety produces purple flowers, as opposed to purple-blue flowers.

Plants of the new cultivar 'SMNBDBT' are similar to plants of the pollen parent, *Buddleia davidii* 'Blue Adonis' in most horticultural characteristics, however, plants of the new cultivar 'SMNBDBT' differ in the following;

1. The new variety is shorter than the pollen parent.
2. The new variety has purple flowers, as opposed to the deep blue flowers of the pollen parent.
3. The new variety has wider leaves than the pollen parent.
4. The new variety has larger flowers than the pollen parent.

COMMERCIAL COMPARISON

Plants of the new cultivar 'SMNBDBT' are comparable to the patended commercial variety *Buddleia* 'Purple Haze' U.S. Plant Pat. No. 24,514. The two *Buddleia* varieties are similar in most horticultural characteristics; however, the new variety 'SMNBDBT' differs in the following:

1. The new cultivar has upright facing flowers, whereas the comparator has flowers facing slightly downward.
2. The new cultivar has tighter flower clusters, whereas the comparator has looser flower clusters.
3. The new cultivar has darker purple flowers than the comparator.

4. The new cultivar has compact and rounded growth habit, whereas the comparator has a compact and spreading growth habit.

Plants of the new cultivar 'SMNBDBT' are comparable to the variety *Buddleia* 'SMNBDPT', co-pending U.S. Plant patent application Ser. No. 15/330,700. The varieties differ from each other primarily in flower color.

BRIEF DESCRIPTION OF THE PHOTOGRAPHS

The accompanying photograph in FIG. 1 illustrates in full color a typical plant of 'SMNBDBT' grown in the ground, at approximately 2 years of age.

Figure 1:
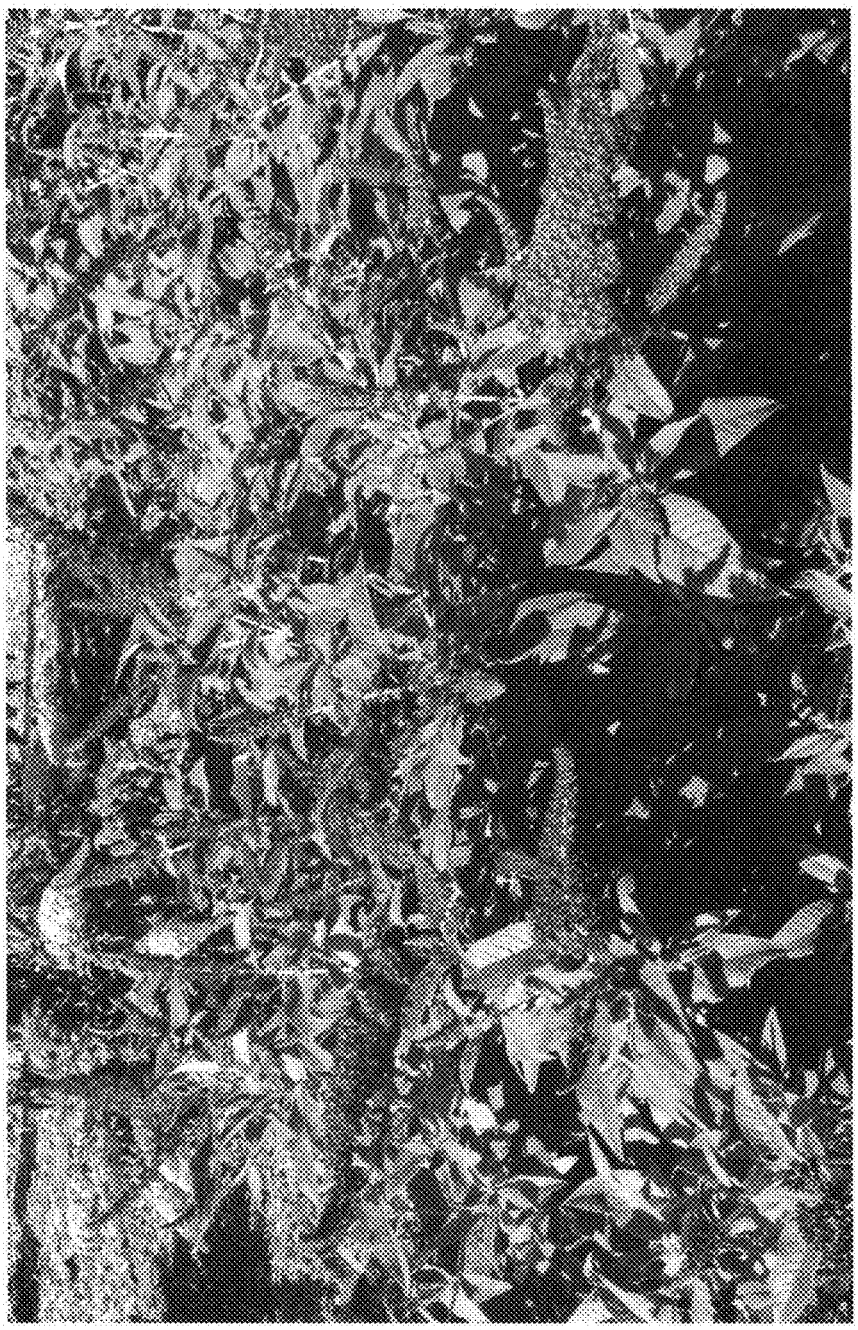
Figure 2:
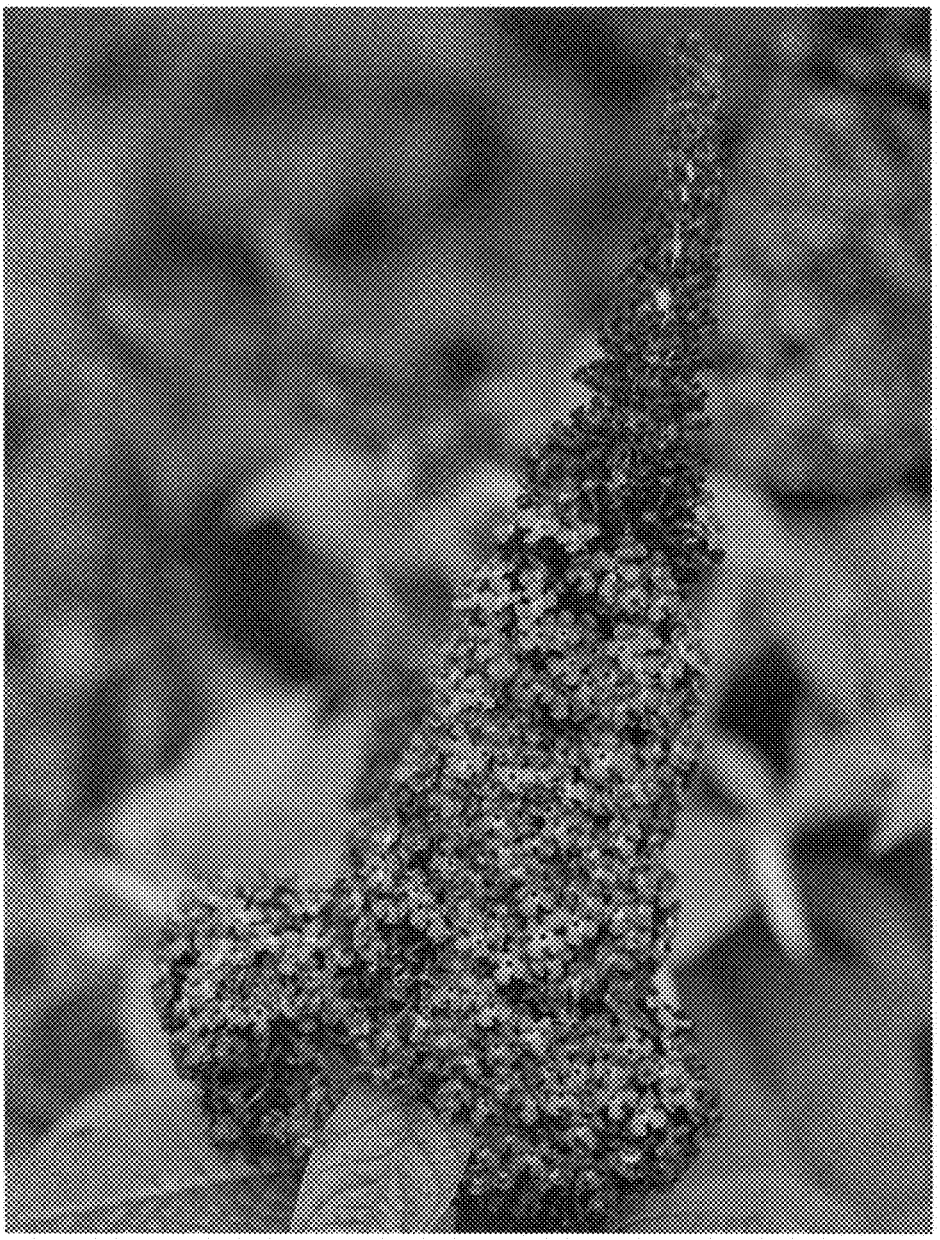
FIG. 2 illustrates an inflorescence of 'SMNBDBT'.
Figure 3:
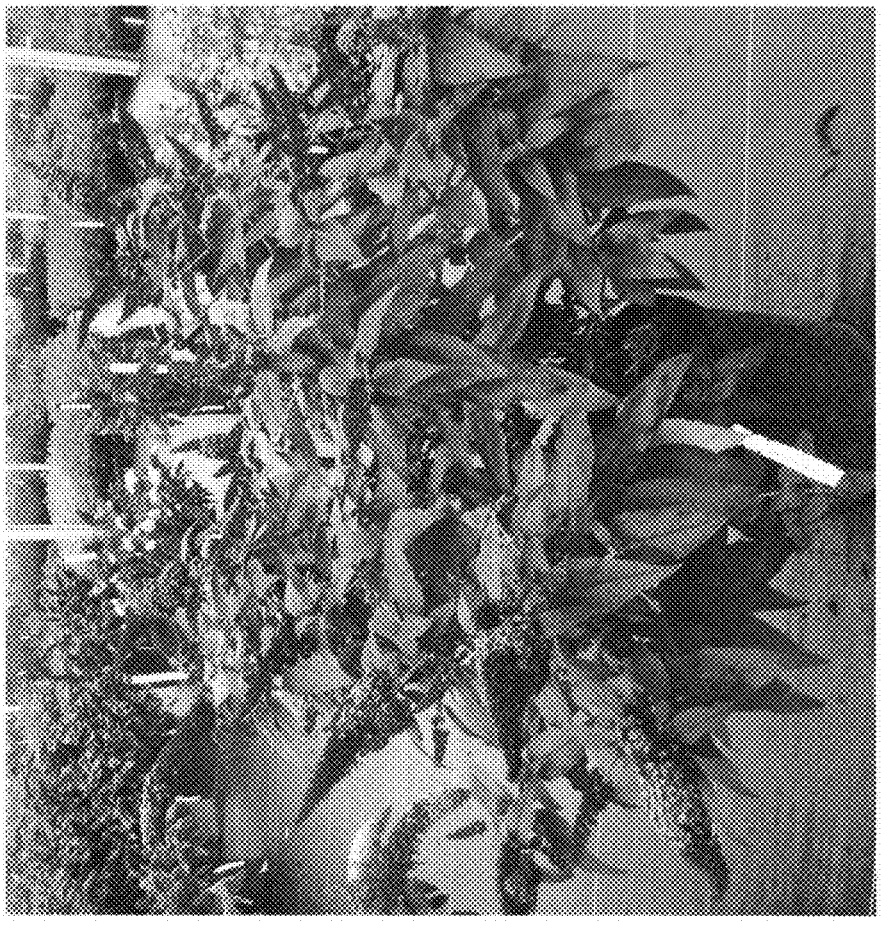
FIG. 3 illustrates a plant of 'SMNBDBT' grown in a nursery, in a 2 gallon pot at approximately 2 years of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SMNBDBT' plants grown in a poly greenhouse during June, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Buddleia davidii* 'SMNBDBT'.

PROPAGATION

Type of propagation typically used: Softwood cutting.

Time to initiate roots: 14-21 days at 21-29° C. average temperature.

Time to produce a rooted young plant: 30 days at 21-29° C. average temperature.

Root description: Dense, free-branching, medium thickness, fibrous. Color is white, not accurately described with R.H.S. chart.

PLANT

Age of plant described: 2-3 years from rooted cutting.

Plant type: Perennial shrub.

Container size of the plant described: Plants in the ground.

Appropriate containers: 1, 2, 3, 5 gallon commercial pots.

Growth habit: Upright.

Overall plant shape: Upright.

Height: Average 52.35 cm.

Plant spread: 88 cm.

Growth rate: Moderate.

Plant vigor: Good.

Characteristics of primary lateral branches:

- *Quantity.*—7.
- *Branching habit.*—Upright and slightly outward.
- *Cross section.*—Square.
- *Length.*—48 cm.
- *Diameter.*—4 cm.
- *Color.*—Near RHS Greyed-Green 195B.
- *Pubescence.*—Present. Dense, short.
- *Stem aspect/angle.*—Approximately 45°.
- *Strength.*—Good.

Internode length: 4 cm.

FOLIAGE

Leaf:

- *Arrangement.*—Opposite, single.
- *Average length.*—11.6 cm.
- *Average width.*—4.2 cm.
- *Shape.*—Lanceolate.
- *Apex.*—Acute.
- *Base.*—Cuneate.
- *Margin.*—Slightly undulate and serrate.
- *Texture of top surface.*—Softly pubescent with distinct veins.
- *Texture of bottom surface.*—Softly pubescent with distinct veins. More pubescent than top surface.
- *Color.*—Young foliage upper side: Near RHS Green 139A. Young foliage under side: Near RHS Greyed-Green 194A. Mature foliage upper side: Near RHS Green 139A. Mature foliage under side: Near RHS Greyed-Green 194A.
- *Venation.*—Type: Pinnate. Venation color upper side: Near RHS Yellow-Green 145A. Venation color under side: Near RHS Yellow-Green 145B.
- *Petiole.*—Length: 3.0 mm. Diameter: 2.0 mm. Color: Upper side: Near RHS Yellow-Green 145A. Lower side: Near RHS Yellow-Green 146C. Texture: Upper side: Soft and pubescent. Lower side: Soft and pubescent.

FLOWER

Flower arrangement: Cone-shaped panicle.

Flower type: Salverform.

Flowering habit: Freely flowering on terminal branches, will develop panicles at other nodes after terminal panicle has bloomed.

Natural flowering season: Mid-summer to early fall.

Inflorescence height:

- *Young.*—15.8 cm.
- *Mature.*—6.05 cm.

Inflorescence width:

- *Young.*—2.0 cm.
- *Mature.*—4.0 cm.

Rate of flower opening: Moderate.

Flower longevity on plant: 3-4 weeks.

Persistent or self-cleaning: Persistent.

Quantity of flowers per inflorescence: Thousands.

Bud:

- *Shape.*—Linear with protruding orbital cap.
- *Length.*—7.0 mm.
- *Diameter.*—1.0 mm.
- *Color.*—Near RHS Violet-Blue 93A.

Flower size:

- *Diameter.*—7.0 mm.
- *Length.*—7.0 mm.
- *Depth (height).*—11.0 mm.

Petals:

- *Appearance.*—Intense and vibrant.
- *Arrangement.*—Whorled.
- *Petal length.*—3.0 mm.
- *Petal width.*—3.0 mm.
- *Quantity.*—4.
- *Texture.*—Smooth and soft.

*Apex*.—Obtuse.
*Shape*.—Oblong to obovate.
*Base*.—Slightly acute.
*Margin*.—Faintly undulate.
*Aspect*.—Outward.

Petal color:
*When opening*.—Upper surface: Near RHS Violet-Blue 93A. Lower surface: Near RHS Violet-Blue 90A with near RHS Violet-Blue 93A along edges.
*Fully opened*.—Upper surface: Near RHS Violet-Blue 93A. Lower surface: Near RHS Violet-Blue 93B with near RHS Violet-Blue 93A along edges.
*Fading to color*.—Upper: Near RHS Violet-Blue 93A. Lower: Near RHS Violet-Blue 93B with near RHS Violet-Blue 93A along edges.

Sepals:
*Quantity per flower*.—4.
*Arrangement*.—Fused into calyx tube.
*Shape*.—Lanceolate to Ovate.
*Length*.—2.0 mm.
*Width*.—0.3 mm.
*Apex*.—Acute.
*Base*.—Cuneate.
*Margin*.—Entire/inconspicuous.
*Texture*.—Upper: Slightly pubescent. Lower: Smooth, slightly pubescent.
*Color*.—Upper Surface: Near RHS Yellow-Green 145C fading to 147C. Lower Surface: Near RHS Yellow-Green 148D.

Calyx:
*Shape*.—Oblong and unguiculate.
*Length*.—3 mm.
*Diameter*.—1 mm.

Peduncle:
*Length*.—1 cm.
*Diameter*.—0.975 cm.
*Angle*.—5-35°.
*Strength*.—Good.
*Texture*.—Smooth, pubescent.
*Color*.—Near RHS Yellow-Green 145B.

Pedicel: Not present.
Fragrance: Light floral fragrance with sweet honey scent.

REPRODUCTIVE ORGANS

Stamens:
*Number*.—4.
*Filament length*.—0.6 mm.
*Filament color*.—Near RHS White 155B, fading to Yellow-Green 145B.

Anthers:
*Shape*.—Lobed.
*Length*.—0.25 mm.
*Color*.—Near RHS White 155B.
*Pollen*.—Quantity: Some. Color: Near RHS Yellow 11C.

Pistil:
*Number*.—1.
*Length*.—1 mm.
*Style*.—Length: less than 1 mm. Color: RHS Yellow-green 145A.
*Stigma*.—Shape: Oblong. Color: Near RHS Yellow-green 145A. Ovary Color: Near RHS Yellow-green 144C.

OTHER CHARACTERISTICS

Seeds and fruits: Not observed to date.
Disease/pest resistance: Neither resistance nor susceptibility to the normal diseases and pests of *Buddleia* observed to date.
Lowest temperature tolerance: To date in trials −31° C.
Highest temperature tolerance: To date in trials 38° C.
Garden performance: Good strong, stout stems hold up well to environmental stressors.

What is claimed is:

1. A new and distinct cultivar of *Buddleia davidii* plant named 'SMNBDBT' as herein illustrated and described.

* * * * *